(12) United States Patent
Nagasawa

(10) Patent No.: US 8,733,669 B2
(45) Date of Patent: May 27, 2014

(54) EFFICACIOUS CONSTITUENT SUPPLY APPARATUS

(75) Inventor: Isamu Nagasawa, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 459 days.

(21) Appl. No.: 13/064,089

(22) Filed: Mar. 4, 2011

(65) Prior Publication Data
US 2011/0233298 A1 Sep. 29, 2011

(30) Foreign Application Priority Data
Mar. 26, 2010 (JP) .................. 2010-072204

(51) Int. Cl.
*A24F 25/00* (2006.01)
*A61L 9/04* (2006.01)

(52) U.S. Cl.
USPC ................ 239/34; 239/49; 239/47; 239/51.5

(58) Field of Classification Search
USPC .................................... 239/34–60
See application file for complete search history.

(56) References Cited

U.S. PATENT DOCUMENTS

| 4,200,229 A * | 4/1980 | Spector ........................... 239/57 |
| 4,940,272 A * | 7/1990 | Weick ........................... 296/97.5 |
| 2010/0243754 A1* | 9/2010 | Harris ............................ 239/34 |

FOREIGN PATENT DOCUMENTS

JP 2006-282085 * 10/2006

* cited by examiner

*Primary Examiner* — Justin Jonaitis
(74) *Attorney, Agent, or Firm* — McGinn IP Law Group, PLLC

(57) ABSTRACT

A cartridge containing aromatic constituents is inserted to an efficacious constituent supply apparatus which is embedded in a door. An insertion slot of the cartridge is formed on a matching surface of the door trim, the surface facing an side surface of an instrument panel. BY forming the insertion slot on the matching surface of the door trim, the insertion slot can be concealed when the door is closed and thus the appearance of the efficacious constituent supply apparatus can be enhanced. In addition, the insertion slot is exposed when the door is opened, working efficiency upon changing the cartridge is not impaired.

5 Claims, 9 Drawing Sheets

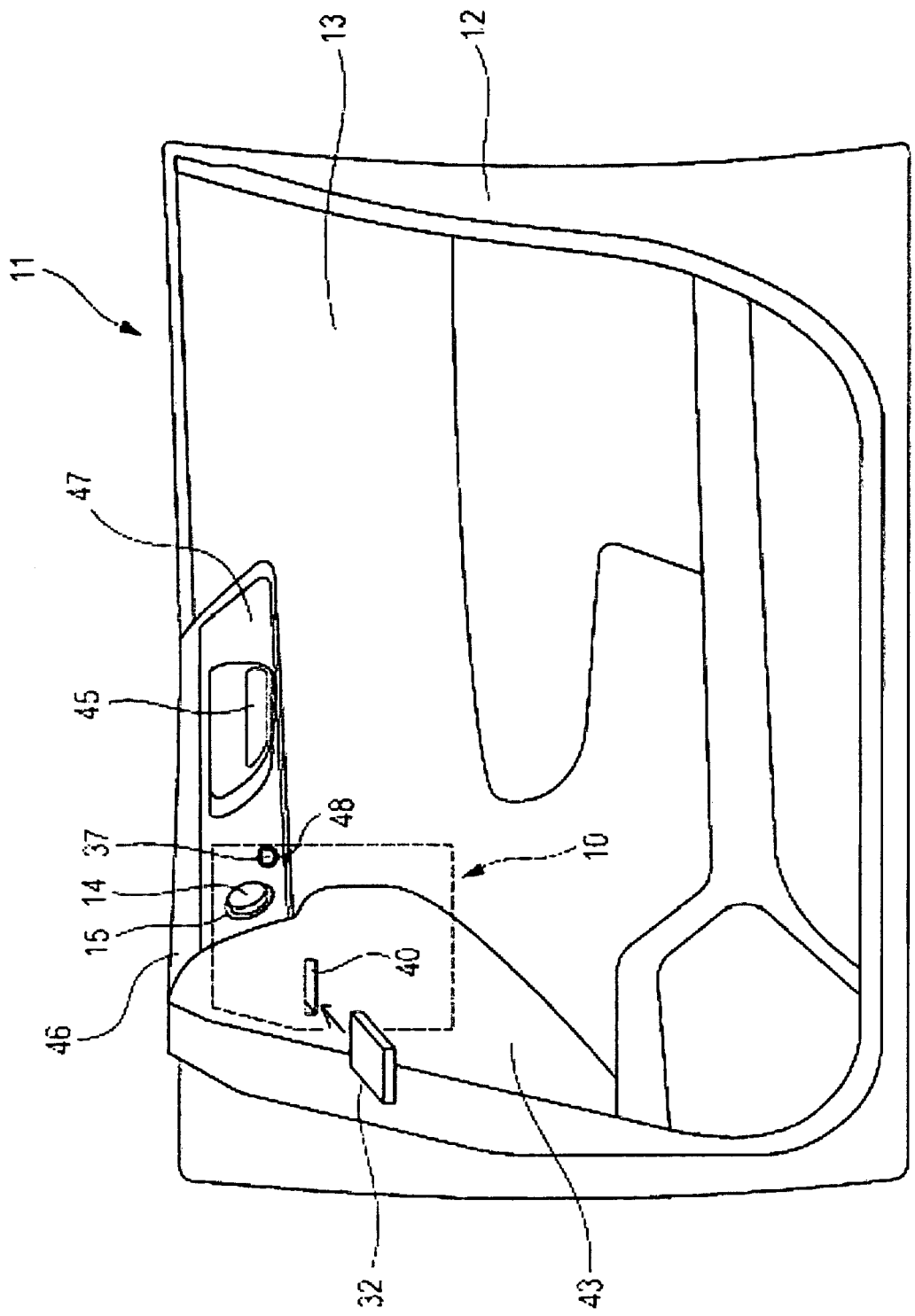

US 8,733,669 B2

EFFICACIOUS CONSTITUENT SUPPLY APPARATUS

CROSS REFERENCES TO RELATED APPLICATIONS

The present application claims priority from Japanese Patent Application No. 2010-072204 filed on Mar. 26, 2010, the entire contents of which are hereby incorporated by reference.

BACKGROUND OF THE INVENTION

1. Field of the Invention

The present invention relates to an efficacious constituent supply apparatus for supplying efficacious constituents.

2. Description of the Related Art

There have been proposed supply apparatuses in which vortex rings of aromatic constituents (efficacious constituents) are projected toward an occupant in order to maintain a good environment within a passenger compartment of a vehicle (refer to, for example, Japanese Unexamined Patent Application Publication No. 2006-282085). Since the apparatuses allow aromatic constituents to be supplied locally, it becomes possible to decrease the usage of aromatic constituents. The supply apparatus according to Japanese Unexamined Patent Application Publication No. 2006-282085 has a plurality of containers in which aromatic constituents are enclosed, and is designed to enhance the satisfaction of a user by switching types of efficacious constituents.

However, the installment of a plurality of containers and valves in the supply apparatus to switch and provide efficacious constituents causes an increase in size and cost of the supply apparatus. Therefore, a supply apparatus is under consideration that encloses efficacious constituents in a cartridge and switches the efficacious constituents by changing the cartridge. For the supply apparatus of this type changing the cartridge, an insertion slot of the cartridge needs to be provided at the supply apparatus. However, the exposed insertion slot impairs the appearance of the supply apparatus.

SUMMARY OF THE INVENTION

The present invention is made in view of the above, and it is an object of the present invention to enhance the appearance of an efficacious constituent supply apparatus that is provided with an insertion slot of a cartridge.

According to an aspect of the present invention, there is provided an efficacious constituent supply apparatus for a vehicle includes a cartridge containing efficacious constituents; an air release unit for releasing air with the efficacious constituents released from the cartridge; and an insertion slot to which the cartridge is inserted, in which the insertion slot is provided at a matching surface of a door trim of the vehicle, facing an instrument panel of the vehicle, or a matching surface of the instrument panel, facing the door trim.

According to another aspect of the present invention, there is provided an efficacious constituent supply apparatus in which the insertion slot is provided at the matching surface of the door trim, while a release hole for releasing air containing efficacious constituents is provided at the door trim.

According to another aspect of the present invention, there is provided an efficacious constituent supply apparatus in which the insertion slot is provided at the matching surface of the instrument panel, while a release hole for releasing air containing efficacious constituents is provided at the instrument panel or a pillar trim.

According to another aspect of the present invention, there is provided an efficacious constituent supply apparatus in witch the insertion slot is concealed by the matching surface of the instrument panel when a door of the vehicle is closed.

According to another aspect of the present invention, there is provided an efficacious constituent supply apparatus in which the insertion slot is concealed by the matching surface of the door trim when a door of the vehicle is closed.

According to the present invention, the insertion slot of the cartridge is formed at the matching surface of the door trim or the instrument panel, whereby it is possible to conceal the insertion slot when a door is closed. As a result, the appearance of the efficacious constituent supply apparatus with the insertion slot can be enhanced.

BRIEF DESCRIPTION OF THE DRAWINGS

FIG. 5 is an explanatory view illustrating an insertion slot of a cartridge which is provided at a door, the view seen from the passenger compartment of the vehicle.

DESCRIPTION OF THE PREFERRED EMBODIMENT

Figure 1:
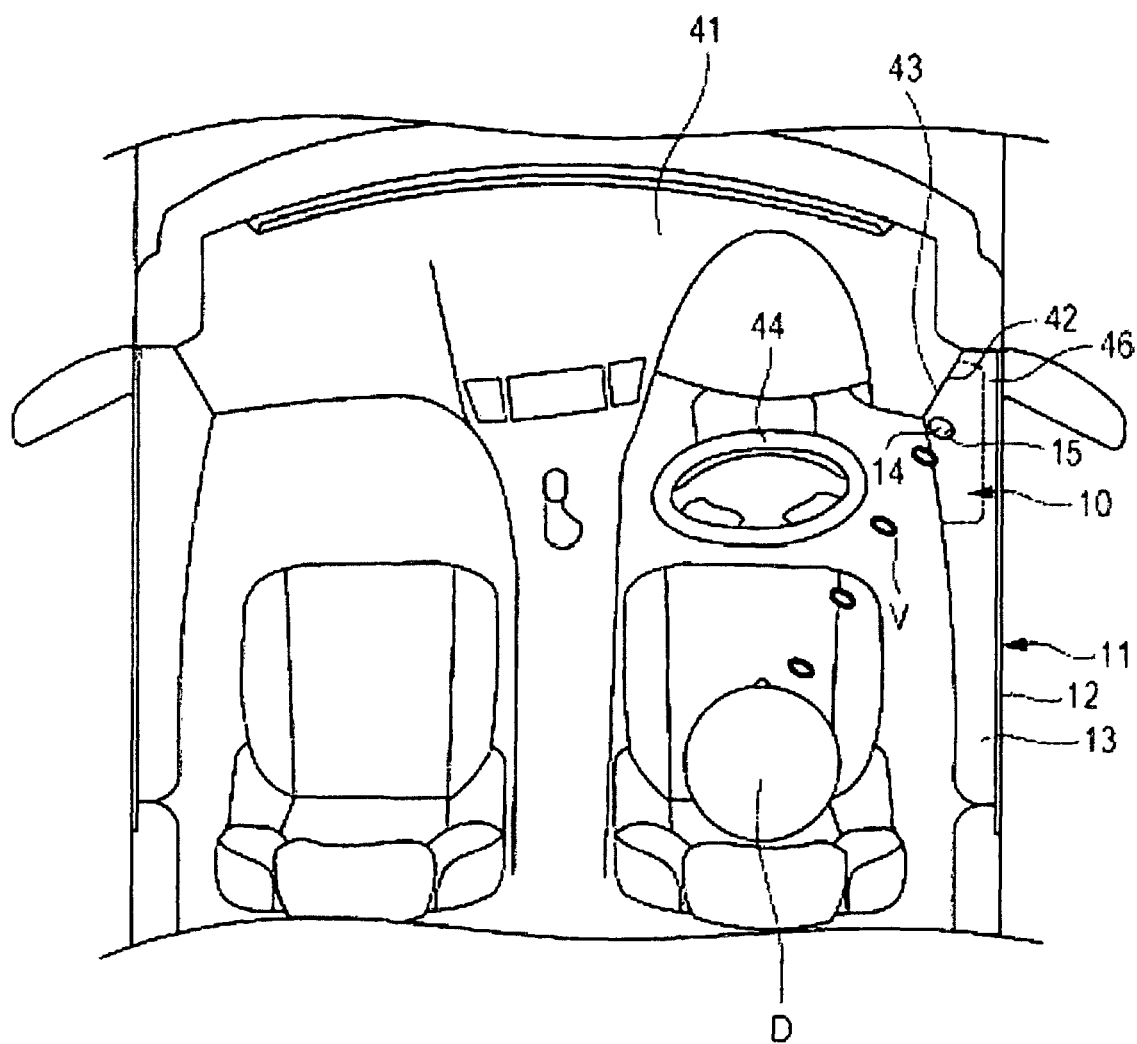
FIG. 1 is an explanatory view illustrating a mounting position of an efficacious constituent supply apparatus which is an embodiment of the present invention, the view seen from the top side of a vehicle.
Figure 2:
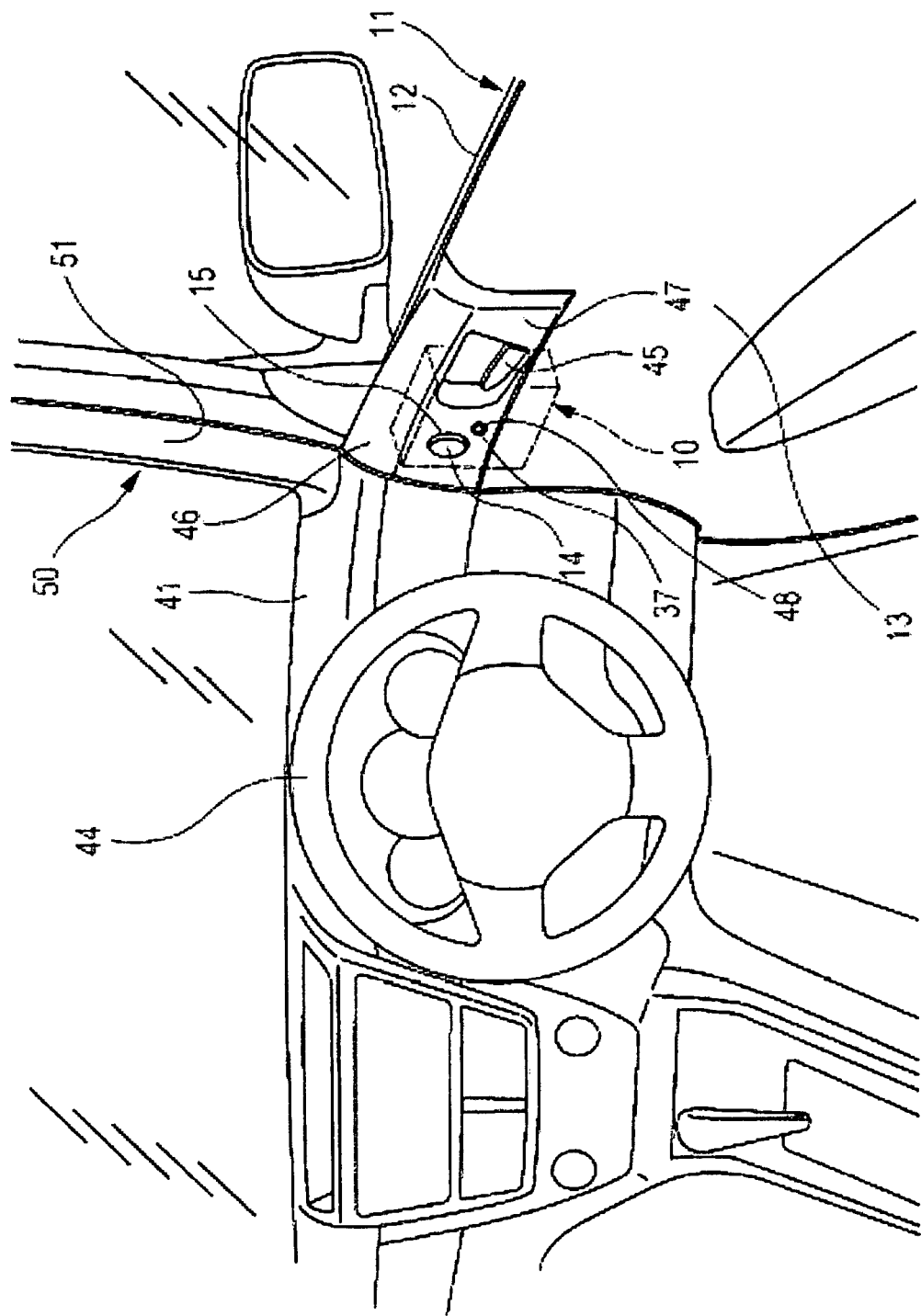
FIG. 2 is an explanatory view illustrating the mounting position of the efficacious constituent supply apparatus, the view seen from the passenger compartment of the vehicle.
Figure 3:
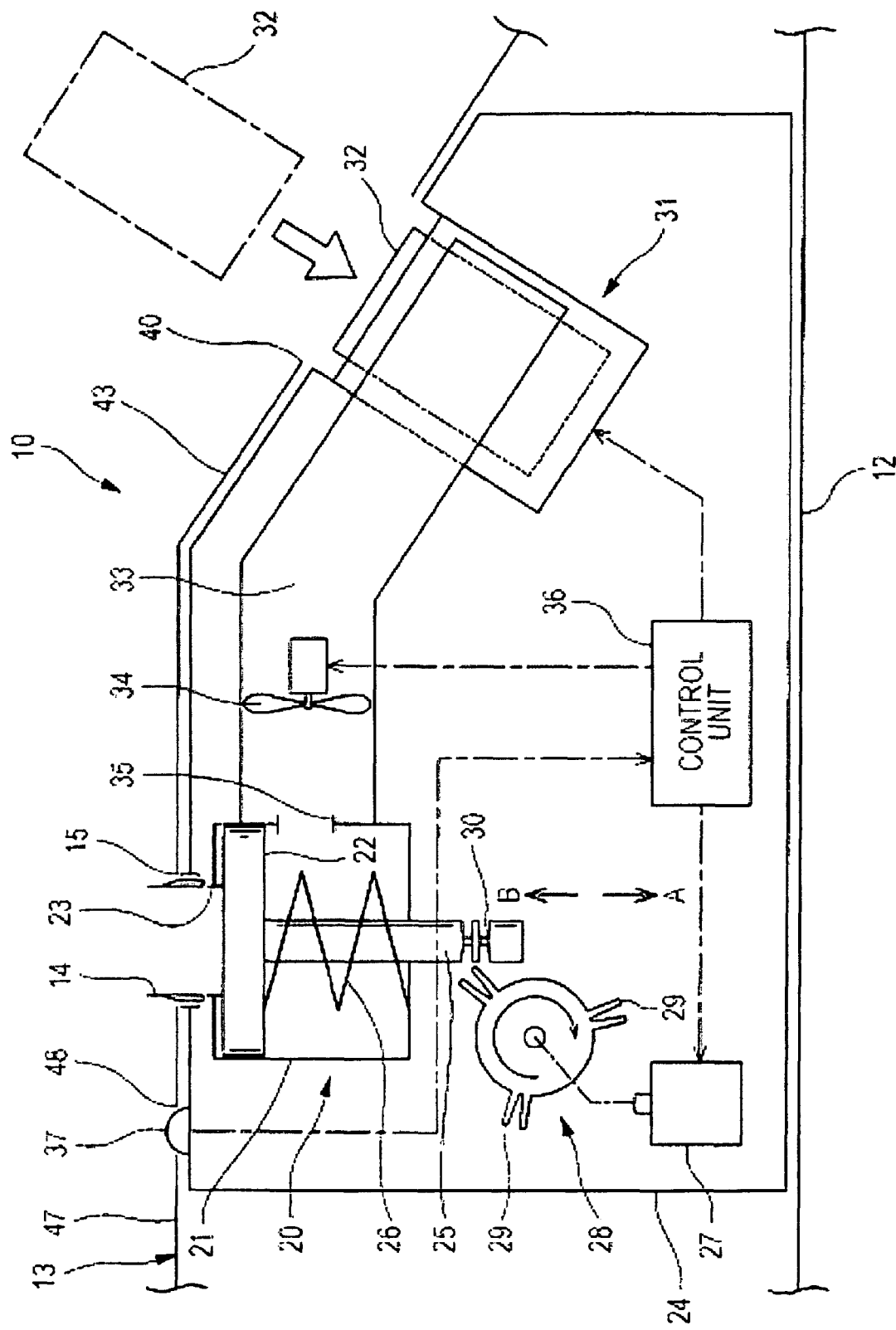
FIG. 3 is a schematic view of an internal structure of the efficacious constituent supply apparatus.

An embodiment of the present invention will hereunder be described with reference to the drawings. FIG. 1 is an explanatory view illustrating a mounting position of an efficacious constituent supply apparatus (hereinafter referred to as supply apparatus) 10 which is an embodiment of the present invention, the view seen from the top side of a vehicle. FIG. 2 is an explanatory view illustrating the mounting position of the supply apparatus 10, the view seen from the passenger compartment of the vehicle. FIG. 3 is a schematic view of an internal structure of the supply apparatus 10.

As shown in FIGS. 1 and 2, a door 11 provided at a vehicle body has a door panel 12 formed with a steel plate or the like and a door trim 13 that is an interior material fixed to the door panel 12. The supply apparatus 10 is embedded in the door 11, and provides aromatic constituents (efficacious constituents) to an occupant D. The supply apparatus 10 is provided with a projecting nozzle 14 as the release hole. The projecting nozzle 14 sticks out to the passenger compartment from a through hole 15 of the door trim 13. As shown in FIG. 1, air containing aromatic constituents is projected as a vortex ring V from the projecting nozzle 14 provided at the door trim 13.

As shown in FIG. 3, the supply apparatus 10 is provided with an air cannon 20 (as an air release unit) that projects the vortex ring V. The air cannon 20 is provided with a cylinder 21 and a piston 22 housed therein. A projecting port 23 is formed at one end of the cylinder 21, and the projecting port 23 and the projecting nozzle 14 are arranged in a concentric pattern. Further, the projecting nozzle 14 is arranged so as to tiltable with respect to a case 24 of the supply apparatus 10. The projecting direction of the vortex ring V can be adjusted by adjusting the direction of the projecting nozzle 14.

A rod member 25 is fixed and a spring member 26 is provided at the backside of the piston 22. The spring member 26 biases the piston 22 toward the projecting port 23. Furthermore, the supply apparatus 10 is provided with a rotating plate 28 that is driven by an electric motor 27. A plurality of engaging claws 29 are formed on the rotating plate 28 at a predetermined interval, and engaging grooves 30 are formed on the rod member 25 so as to correspond to the engaging claws 29. Accordingly the reciprocating movement of the piston 22 can be achieved by rotating the rotating plate 28, and air in the cylinder 21 can be projected as the vortex ring V from the projecting port 23. More specifically, the engaging claws 29 are engaged with the engaging grooves 30 by rotating the rotating plate 28 to drag the piston 22 into a receded position in the direction of an arrow A, and then the engaging claws 29 are disengaged from the engaging grooves 30 to extrude the piston 22 to an advanced position in the direction of an arrow B.

The supply apparatus 10 is provided with an aroma container 31 in order to fill the cylinder 21 of the air cannon 20 with aromatic constituents, and a cartridge 32 containing aromatic constituents is inserted into the aroma container 31. The aroma container 31 is provided with an electric heater (not shown) and the cartridge 32 encloses a sponge or the like impregnated with aromatic constituents. When the electric heater of the aroma container 31 is energized, the cartridge 32 is heated and aromatic constituents can be promoted to evaporate. On the other hand, when the energization of the electric heater of the aroma container 31 is halted, the cartridge 32 is cooled and the evaporation of aromatic constituents can be suppressed. The structure of the cartridge 32 containing aromatic constituents is not limited to the one described above, and a capsule enclosing aromatic constituents may be provided to the cartridge 32 and may be torn to release the aromatic constituents.

A channel housing 33 is provided between the aroma container 31 and the cylinder 21, the channel housing guiding air from the aroma container 31 to the cylinder 21. A fan 34 is mounted in the channel housing 33 in order to flow air from the aroma container 31 to the cylinder 21. Further, an inlet port 35 is formed at a side of the cylinder 21, through which the cylinder 21 and the channel housing 33 are communicated with each other. The cylinder 21 can be filled with aromatic constituents generated at the aroma container 31 by driving the fan 34.

The supply apparatus 10 is provided with a control unit 36 to control the air cannon 20, the aroma container 31 and the fan 34. The control unit 36 includes a not-shown microprocessor (CPU), and a ROM, a RAM and an I/O port are connected to the CPU via bus lines. A control program and various data are stored in the ROM, and data which have been processed in the CPU is temporarily stored in the RAM. In addition, a projection switch 37 to be operated by the occupant D upon projecting the vortex ring V is connected to the control unit 36.

Figure 4A:
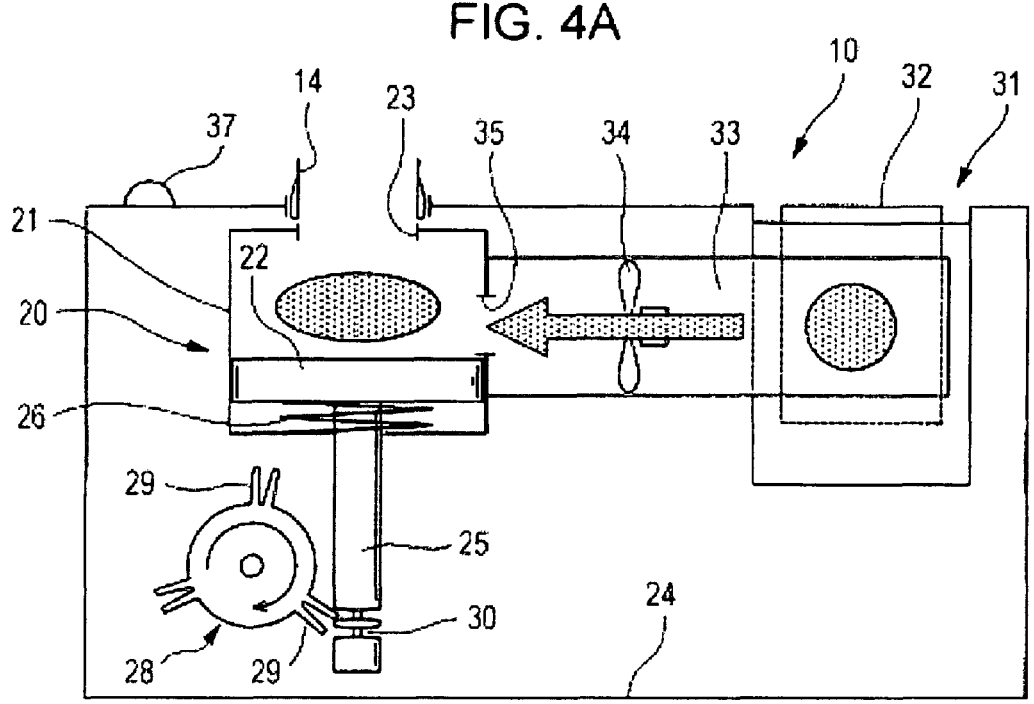
FIGS. 4A and 4B are explanatory views illustrating operation states of the efficacious constituent supply apparatus.
Figure 4B:
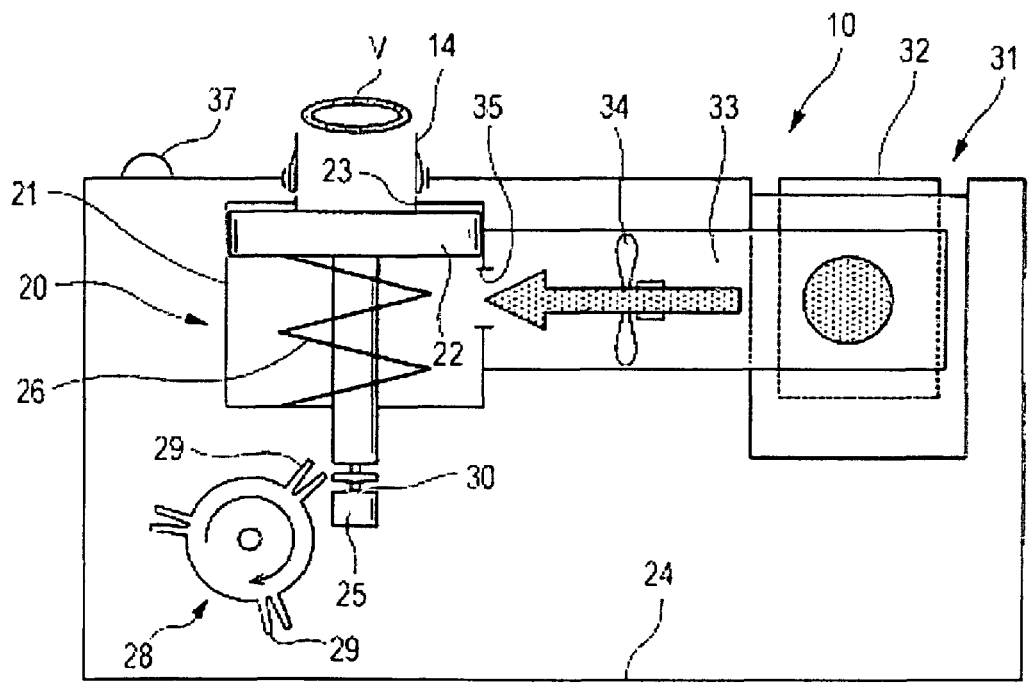

Next, operation states of the supply apparatus 10 upon projecting the vortex ring V will be described. FIGS. 4A and 4B are explanatory views illustrating the operation states of the supply apparatus 10. As shown in FIG. 4A, when the occupant D presses the projection switch 37, the fan 34 is driven while generating aromatic constituents at the aroma container 31, and the aromatic constituents are continuously provided toward the cylinder 21. Under this state the vortex ring V containing aromatic constituents can be continuously projected by rotating the rotating plate 28 to reciprocate the piston 22, as shown FIGS. 4A and 4B. Instead of projecting the vortex ring V from the projecting port 23, air may be continuously released from the projecting port 23. In this case, the rotating plate 28 is halted at a predetermined position, whereby the piston 22 is held at the receded position shown in FIG. 4A. As a result, the inlet port 35 and the projecting port 23 are communicated with each other in the cylinder 21, and thus air containing aromatic constituents can be continuously released from the projecting port 23.

Figure 6:
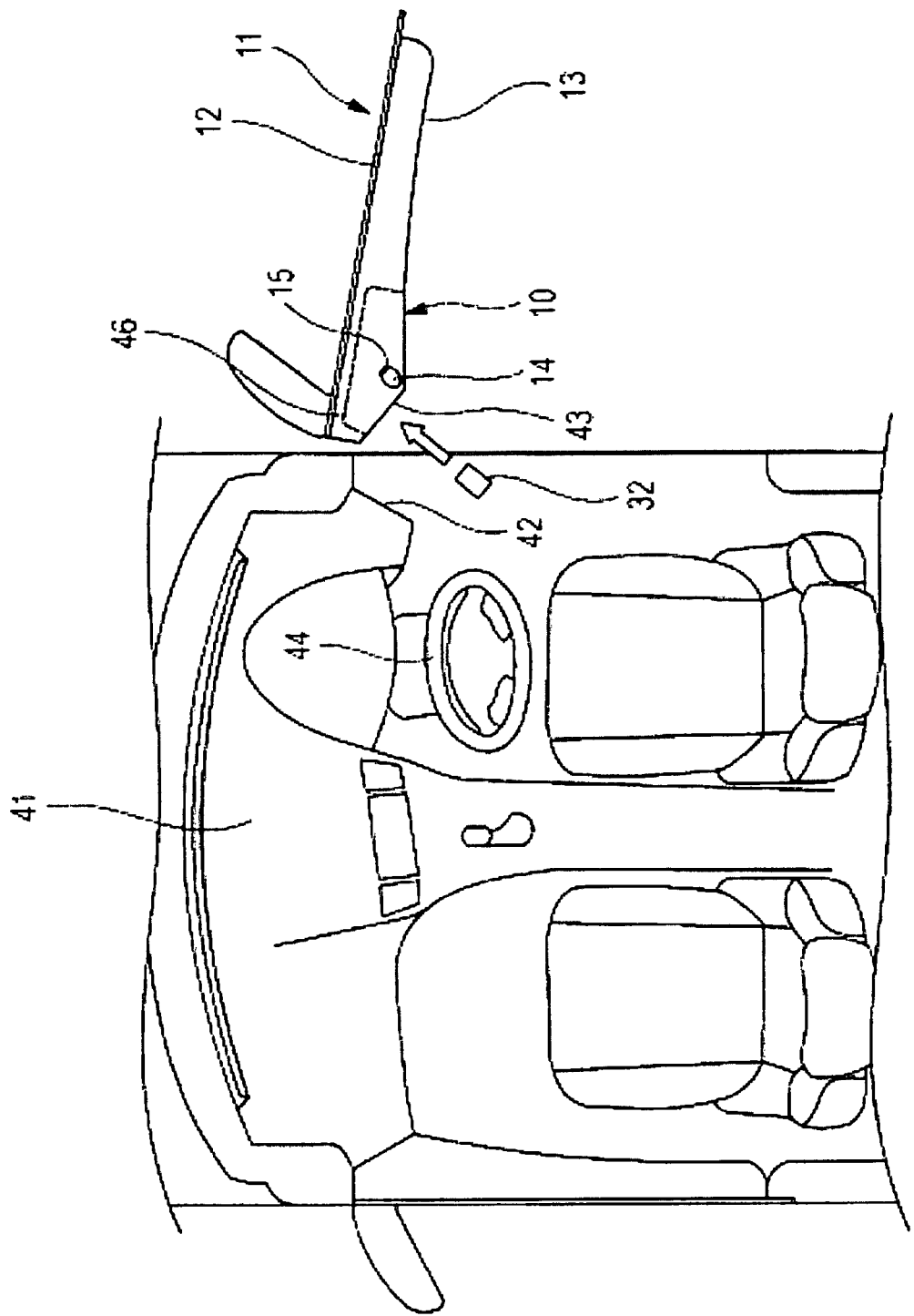
FIG. 6 is an explanatory view illustrating an inserting position of the cartridge, the view seen from the top side of a vehicle.

Next, an insertion slot 40 of the cartridge 32 will be described. FIG. 5 is an explanatory view illustrating an insertion slot 40 of the cartridge 32 which is formed at a door 11. FIG. 6 is an explanatory view illustrating an inserting position of the cartridge 32, the view seen from the top side of the vehicle. As shown in FIGS. 5 and 6, the insertion slot 40 is provided at a matching surface 43 of the door trim 13 facing a side surface 42 of an instrument panel 41. Since the insertion slot 40 is formed at the matching surface 43 of the door trim 13 as just described, the insertion slot 40 can be concealed when the door 11 is closed, as shown in FIGS. 1 and 2. As a result, the appearance of the supply apparatus 10 can be enhanced. In addition, the insertion slot 40 can be exposed by opening the door 11, and thus working efficiency upon changing the cartridge 32 is not impaired.

Since the projecting nozzle 14 is mounted at the door trim 13, the vortex ring V can be projected toward the occupant D without being interrupted by a steering wheel 44 or the like. In addition, since the projecting nozzle 14 and the projection switch 37 are mounted at the door trim 13, the occupant D can operate the projecting nozzle 14 and the projection switch 37 without changing his/her sitting posture. Especially in the illustrated case, the projecting nozzle 14 and the projection switch 37 can be operated very easily since the projecting nozzle 14 and the projection switch 37 are mounted in proximity to an opening/closing lever 45 to be operated for opening and closing the door 11.

In addition, since the supply apparatus 10 is housed in the inside of the door trim, which can be easily detached, the supply apparatus 10 can be easily installed on a fully assembled vehicle. Furthermore, since it is easy to obtain a mounting space at a front portion 46 of the door 11, the supply apparatus 10 can be easily employed. More specifically, since, as shown in FIG. 1, the door trim 13 overhangs to the passenger compartment side at the front portion 46 of the door 11 which is adjacent to the instrument panel 41, a large space can be obtained between the door trim 13 and the door panel 12. Since a large space can be obtained at the front portion 46 of the door trim as just described, the supply apparatus 10 can be easily embedded. Note that the supply apparatus 10 is fixed with respect to a reinforcement member of the door 11, the door panel 12 or the like.

Moreover, as shown in FIGS. 2 and 5, a decorative panel 47 is provided in proximity to the opening/closing lever 45 of the door trim 13, and the through hole 15 for the projecting nozzle 14 and a through hole 48 for the projection switch 37 are formed in the decorative panel 47. Accordingly, when the supply apparatus 10 is installed on a fully assembled vehicle, not the entire door trim 13, but the decorative panel 47, which is a constitutive part of the door trim 13, is replaced. Since the number of parts needing replacement is limited to a minimum as just described, the cost for installing the supply apparatus 10 can be suppressed. Note that the door trim 13 and the decorative panel 47 may be furnished with the through holes 15 and 48 when the supply apparatus is installed on a fully assembled vehicle.

Figure 7:
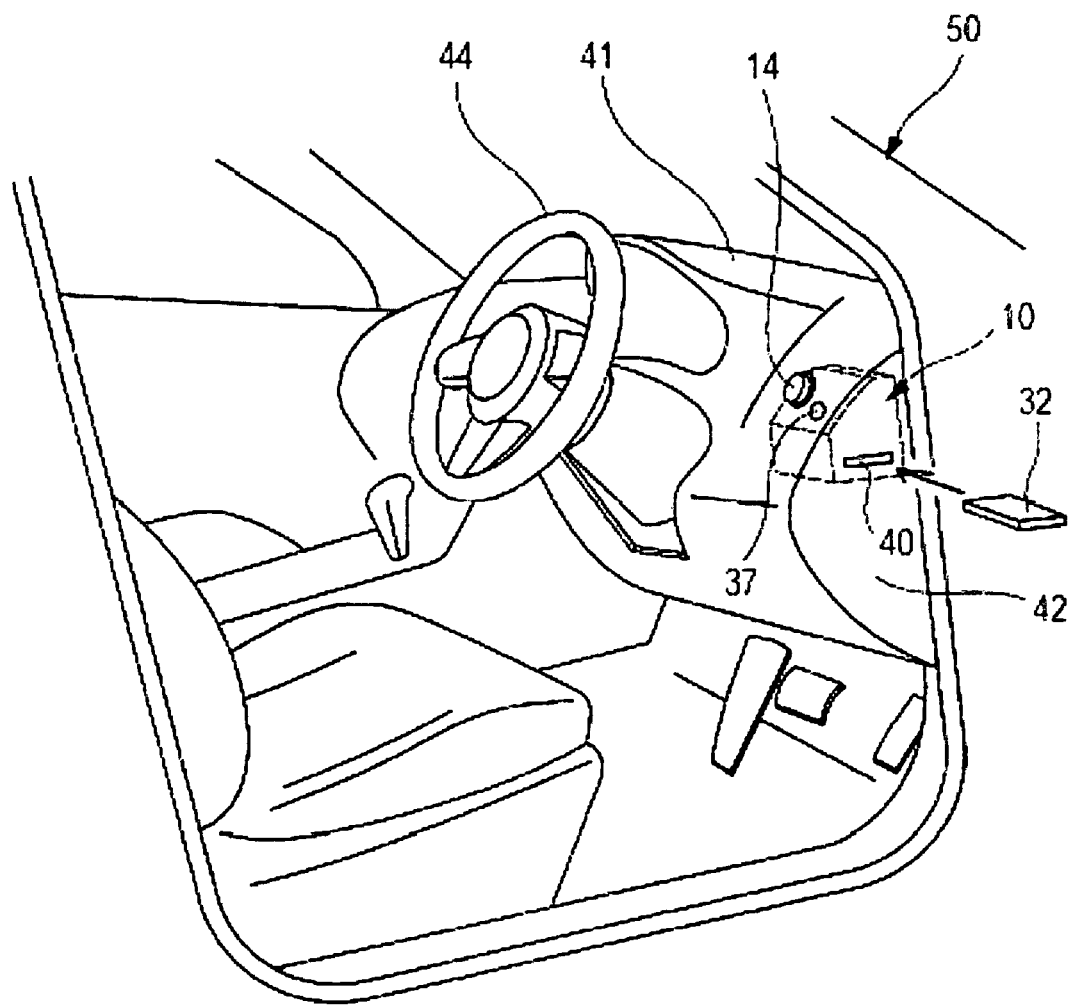
FIG. 7 is an explanatory view illustrating another mounting position of the efficacious constituent supply apparatus, the view seen from the outside of the vehicle.
Figure 8:
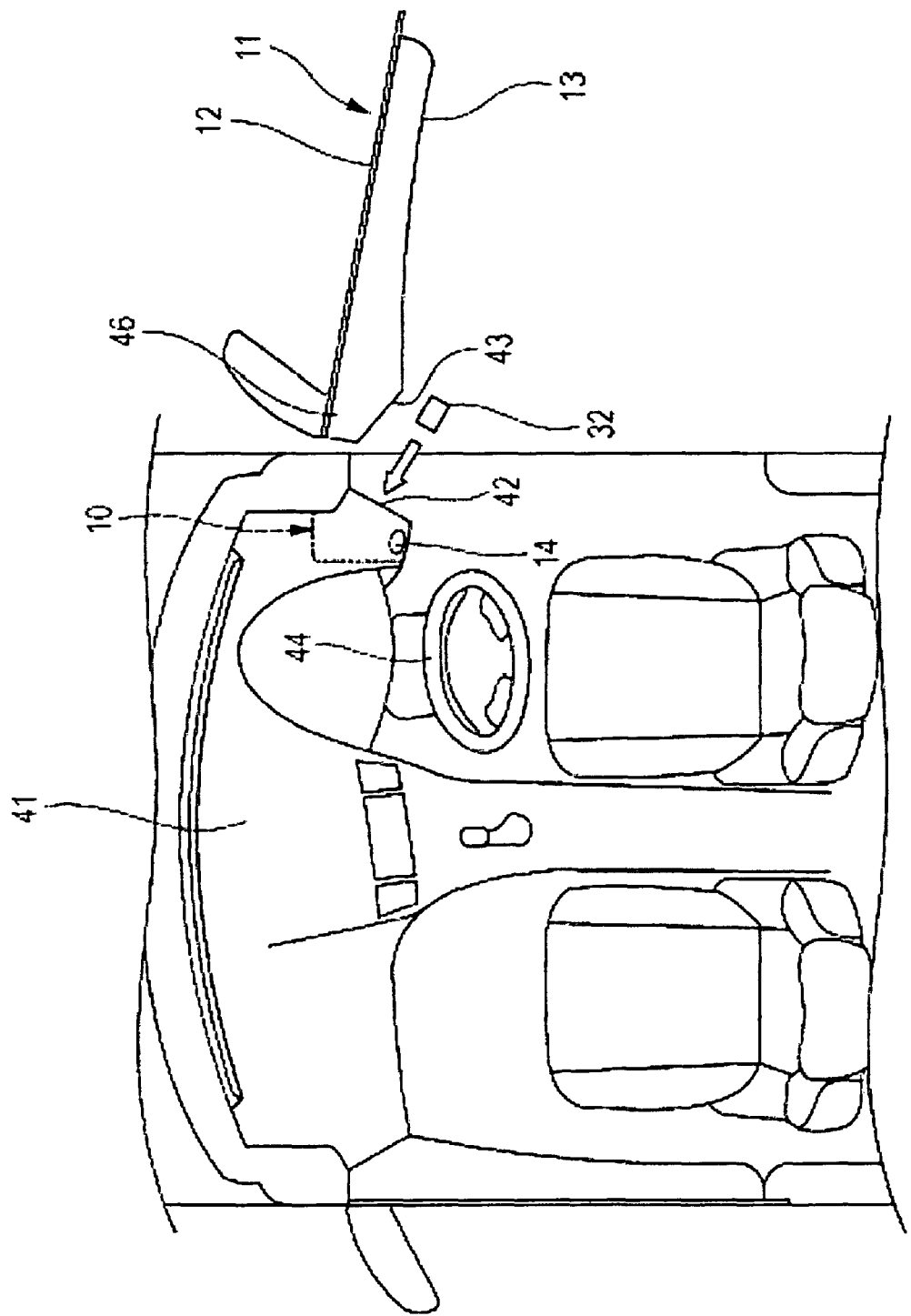
FIG. 8 is an explanatory view illustrating the other mounting position of the efficacious constituent supply apparatus, the view seen from the topside of the vehicle.
Figure 9:
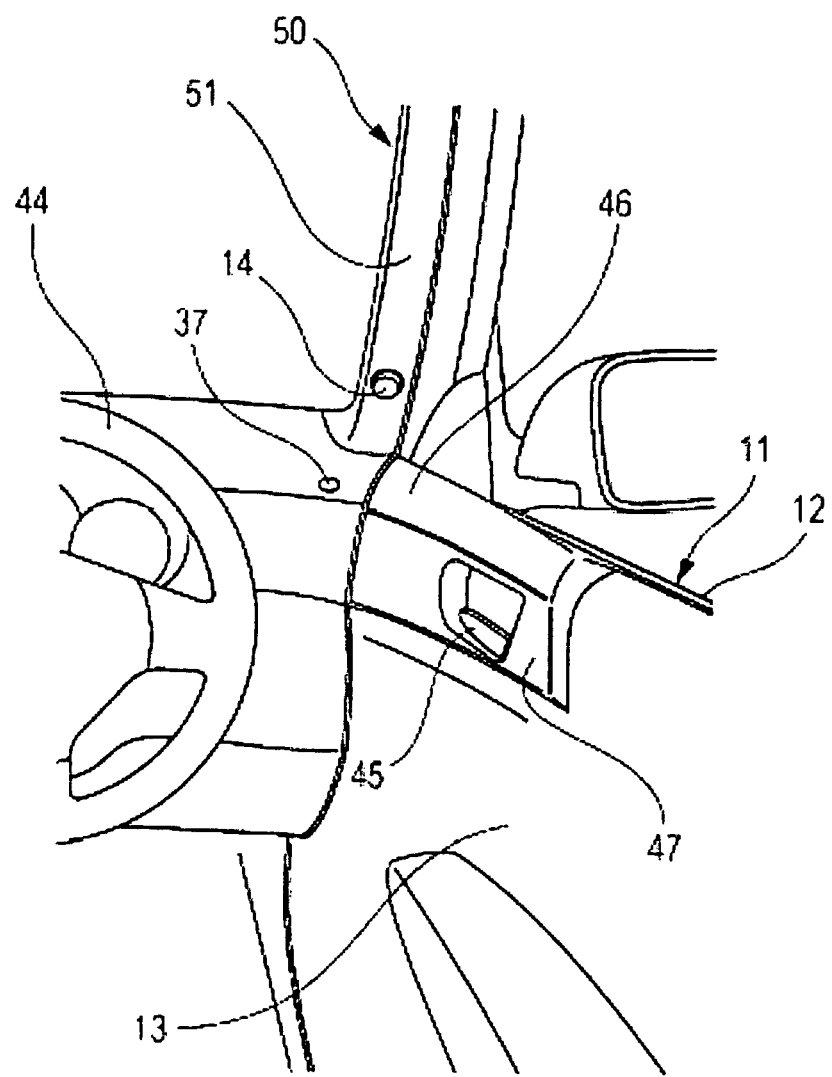
FIG. 9 is an explanatory view illustrating a mounting position of a projecting nozzle.

While the supply apparatus 10 is embedded in the door 11 in the above description, the present invention is not limited to this, and the supply apparatus 10 may be embedded in the instrument panel 41. FIG. 7 is an explanatory view illustrating another mounting position of the supply apparatus 10, the view seen from the outside of the vehicle. FIG. 8 is an explanatory view illustrating the other mounting position of the supply apparatus 10, the view seen from the topside of the vehicle. FIG. 9 is an explanatory view illustrating a mounting position of the projecting nozzle 14.

As shown FIGS. 7 and 8, the supply apparatus 10 is embedded in the instrument panel 41, and the insertion slot 40 is provided at the side surface (matching surface) 42 of the instrument panel 41, the surface facing the door trim 13. Even in the case that the insertion slot 40 is provided at the side surface 42 of the instrument panel 41 as just described, the insertion slot 40 can be concealed when the door 11 is closed. As a result, the appearance of the supply apparatus 10 can be enhanced. In addition, the insertion slot 40 can be exposed by opening the door 11, and thus working efficiency upon changing the cartridge 32 is not impaired. In the case that the supply apparatus 10 is embedded in the instrument panel 41 as described above, the projecting nozzle 14 and the projection switch 37 are provided at the instrument panel 41. The projecting nozzle 14 may be mounted at any position as long as the vortex ring V is not interrupted by the steering wheel 44 or the like, as mentioned above. For example, as shown in FIG. 9, the projecting nozzle 14 may be mounted at a pillar trim 51 which is installed on a front pillar 50.

The present invention is not limited to the above-mentioned embodiments and various changes may be made without departing from the scope of the invention. For example, while aromatic constituents are provided as the efficacious constituents in the foregoing description, the efficacious constituents are not limited to aromatic constituents, and a capsaicin constituent, an isothiocyanate constituent and the like having an awakening effect may be provided as efficacious constituents. In addition, while the supply apparatus 10 is embedded in the door 11 or the instrument panel 41 at a driver side in the foregoing description, the present invention is not limited to this, and the supply apparatus 10 may be embedded in a door or an instrument panel at a front passenger side.

In addition, while the piston 22 is driven by the electric motor 27 in the illustrated case, the present invention is not limited to this, and the piston 22 may be driven by a combination of an electromagnetic coil and a moving iron core. Furthermore, the air cannon 20 may be configured with a diaphragm, without the piston 22. The present invention is also effectively applicable to a supply apparatus that does not provide aromatic constituents by the vortex ring V, but simply releases air containing aromatic constituents.

What is claimed is:

1. An efficacious constituent supply apparatus for a vehicle comprising;
   a cartridge containing efficacious constituents;
   an air release unit for releasing air with the efficacious constituents released from the cartridge;
   a case;
   an insertion slot to which the cartridge is inserted; and
   a door for an occupant for getting into and out of the vehicle,
   wherein the air release unit has a projecting nozzle for releasing air with the efficacious constituents,
   wherein the insertion slot and the projecting nozzle are arranged together in the case of the supply apparatus,
   wherein the insertion slot is provided at a matching surface of a door trim of the vehicle, facing a side surface of an instrument panel of the vehicle, or a matching surface of the instrument panel, facing a side surface of the door trim, and
   wherein the matching surface of the door trim of the vehicle and the side surface of the instrument panel of the vehicle, or the matching surface of the instrument panel and the side surface of the door trim, face each other when the door is closed.

2. The efficacious constituent supply apparatus according to claim 1, wherein the insertion slot is provided at the matching surface of the door trim, and a release hole for releasing air containing efficacious constituents is provided at the door trim.

3. The efficacious constituent supply apparatus according to claim 1, wherein the insertion slot is provided at the matching surface of the instrument panel, and a release hole for releasing air containing efficacious constituents is provided at the instrument panel or a pillar trim.

4. The efficacious constituent supply apparatus according to claim 1, wherein the insertion slot is concealed when the door of the vehicle is closed.

5. The efficacious constituent supply apparatus according to claim 1, wherein the insertion slot is exposed when the door of the vehicle is opened.

* * * * *